United States Patent
Varpula et al.

[11] Patent Number: 6,049,211
[45] Date of Patent: Apr. 11, 2000

[54] METHOD AND APPARATUS FOR DETERMINATION OF FIBER ORIENTATION IN PAPER OR PAPERBOARD WEB

[75] Inventors: Timo Varpula, Vantaa; Heikki Seppä, Helsinki, both of Finland

[73] Assignee: Valmet Automation, Helsinki, Finland

[21] Appl. No.: 08/981,378

[22] PCT Filed: May 29, 1996

[86] PCT No.: PCT/FI96/00306

§ 371 Date: Dec. 18, 1997

§ 102(e) Date: Dec. 18, 1997

[87] PCT Pub. No.: WO97/01088

PCT Pub. Date: Jan. 9, 1997

[30] Foreign Application Priority Data

Jun. 21, 1995 [FI] Finland ................................. 953114

[51] Int. Cl.[7] ................................................. G01N 22/00
[52] U.S. Cl. ........................ 324/636; 324/631; 324/633
[58] Field of Search ................................. 324/631, 632, 324/633, 634, 635, 636; 73/159–160

[56] References Cited

U.S. PATENT DOCUMENTS

| | | | |
|---|---|---|---|
| 4,710,700 | 12/1987 | Osaki et al. | 324/631 |
| 4,781,063 | 11/1988 | Osaki et al. | 324/631 |
| 4,841,223 | 6/1989 | Baum et al. | 324/631 |
| 4,885,527 | 12/1989 | Lacombe et al. | 324/636 |
| 4,904,928 | 2/1990 | Lewis | 324/636 |
| 4,943,778 | 7/1990 | Osaki | 324/636 |

*Primary Examiner*—Diep N. Do
*Attorney, Agent, or Firm*—Cohen, Pontani, Lieberman & Pavane

[57] ABSTRACT

A method and apparatus for determination of orientation of fibers in a material such as a paper or paperboard web comprised of elongated fibers of high moisture content. The material is subjected to an alternating electric field (E) of the RF or microwave frequency range lying in the plane of the material and the change caused by the presence of the material in the alternating electric field (E) is measured. The direction of the alternating electric field (E) is altered during the measurement, whereby the material need not be rotated with respect to the resonator for the measurement.

24 Claims, 5 Drawing Sheets

METHOD AND APPARATUS FOR DETERMINATION OF FIBER ORIENTATION IN PAPER OR PAPERBOARD WEB

FIELD OF THE INVENTION

The present invention relates to a method and apparatus for determination of fiber orientation (i.e., orientation angle and orientation ratio) in paper or paperboard web.

The method and apparatus disclosed herein can be used on-line on a paper or paperboard web forming machine for a noncontacting determination of fiber orientation ratio and orientation angle in the paper or paperboard web. Obviously, the apparatus may also be used in a laboratory for determination of fiber orientation ratio and angle.

BACKGROUND OF THE INVENTION

In the prior art, no reliable method has been available for on-line measurement of fiber orientation. However, fiber orientation ratio and orientation angle are critical parameters of a paper web. Fiber orientation affects the strength properties of paper and paperboard: the tensile strength of the web is higher for tension in parallel with the fibers than in a direction perpendicular to the fibers. Also the runnability of the paper in a printing machine or copier is dependent on the fiber orientation. A paper grade having an unfavourable fiber orientation angle and orientation ratio tends to curl and shrink in an undesirable manner.

In a paper machine, fiber orientation in web formation is most crucially affected by the difference between the wire speed and the jet exit velocity from the headbox slice. If this speed difference, or the draw, is greater than zero, the fibers tend to orient themselves predominantly in the machine direction, whereby the tensile strength of the web increases in the machine direction as is desirable in most cases. If the jet velocity at the headbox slice contains a cross-machine component, the main orientation direction of fibers may deviate from the machine direction, whereby the fiber orientation angle becomes different from zero. By definition, fiber orientation ratio is the difference between orientations in the cross-machine and machine directions. When measured as the tensile strength in these two main directions, the ratio generally is from 2 to 3.

Fiber orientation can be measured off-line using a conventional method based on laser light. In this method, the paper web surface is illuminated with a circular pencil beam of laser light. On the paper surface, the laser light spot assumes an elliptical shape, because the fibers that are principally oriented in the machine direction of the formed web have different optical properties along the fibers from those measured orthogonally to the fibers. The length ratio of the major axes of the ellipse is proportional to the fiber orientation ratio and the angle of rotation of the major axis of the ellipse with regard to the machine direction is proportional to the orientation angle. While the method has found use in off-line laboratory measurements, it has not been reliably adapted to on-line measurements. Furthermore, under on-line conditions the method is hampered, among other things, by the sensitivity of the optics to soiling, the small size of the laser light spot and the difficulty in focusing the optics onto a fluttering web. Moreover, the method is applicable only to thin-caliper paper grades that are light-transmissive.

Also known in the art is a method in which the Young's modulus of the paper web is measured by means of ultrasound in both the machine and cross-machine directions. The method is based on the dependence of the acoustic wave propagation speed in different directions along the web on the orientation of fibers. This method has not been adapted to on-line measurements, and under laboratory conditions the results are dependent, besides fiber orientation, also on the internal stresses of the bonded fibers. On-line application of this method is complicated by the rapid pressure variations of the ambient air that occur on the surface of a fast-moving web. Furthermore, since the method requires physical contact with the web, its suitability to on-line measurement is severely limited.

Fiber orientation is also determined by means of a conventional method based on the measurement of tensile strength in the machine and cross-machine directions using elongation test equipment. This method is applicable to off-line measurement of paper samples only.

Still another method of orientation determination is based on imaging the surface of the paper web after staining of a portion of the superficial fibers. This method is clumsy and reveals the orientation of the superficial fibers only.

SUMMARY OF THE INVENTION

It is an object of the present invention to overcome the drawbacks of the above-described techniques and to provide an entirely novel method and apparatus for determination of fiber orientation in a web of high moisture content.

The goal of the present invention is achieved by subjecting a moist, planar material comprised of fibers such as a paper or paperboard web to a planar electromagnetic field of the RF or microwave frequency range, whereby the wavefront of the electromagnetic field is arranged parallel with the plane of the web, thus making it possible to measure the fiber orientation of said planar material without altering the orientation of the material with respect to the sensor head of the measurement equipment. Thence, the fiber orientation of, e.g., a paper web running in a paper machine can be measured. In a preferred embodiment of the present invention, the direction of the electromagnetic radiofrequency field is altered and the dielectric losses caused by the electric polarization in the material under measurement are measured as a function of the electric field polarization. In an alternative embodiment of the method, the angular direction change of the polarization vector caused by the oriented fibers of the material is measured using a radiofrequency electric field of constant field strength. In a third alternative embodiment of the method, the losses in the material are measured simultaneously by virtue of three standing-wave modes in a split, rectangular cavity resonator. While the RF electromagnetic field of each mode is arranged parallel to the plane of the web, each mode has a different polarization. The first mode has the electric field oriented in the x-direction, the second mode in the y-direction and the third mode has a radial orientation. Thence, the third mode serves to detect the average dielectric loss in the paper web. By computing the ellipse of fiber orientation from the losses measured using the different standing-wave modes, the fiber orientation (that is, orientation angle and ratio) can be determined.

An essential characteristic of the method according to the present invention is that the fiber orientation of a planar material to be measured such as a paper web is determined without rotating the material with respect to the sensor head of the measurement equipment. This is a significant advantage with respect to prior-art techniques and facilitates the application of the method to on-line measurements on paper machines, for instance.

The present invention offers significant benefits.

As the present invention is based on the measurement of dielectric losses in the water bound in aggregated fibers, it is insensitive to, e.g., internal stresses of the bonded fibers. Hence, the present invention facilitates noncontacting on-line measurement, which can vastly contribute to process control in, e.g., the paper industry.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the following, the present invention will be examined in more detail by means of exemplifying embodiments with reference to the attached drawings, in which:

FIG. 2b shows a top view of the cavity resonator of FIG. 2a;

FIG. 3b shows a top view of the cavity resonator of FIG. 3a;

DETAILED DESCRIPTION OF THE PRESENTLY PREFERRED EMBODIMENTS

Figure 1A:
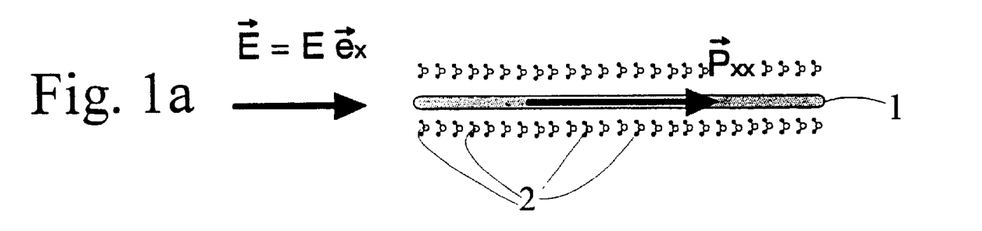
FIGS. 1a–1c show a cellulose fiber with water molecules bound thereto in different orientations with respect to an external electric field in the method according to the present invention.
Figure 1B:
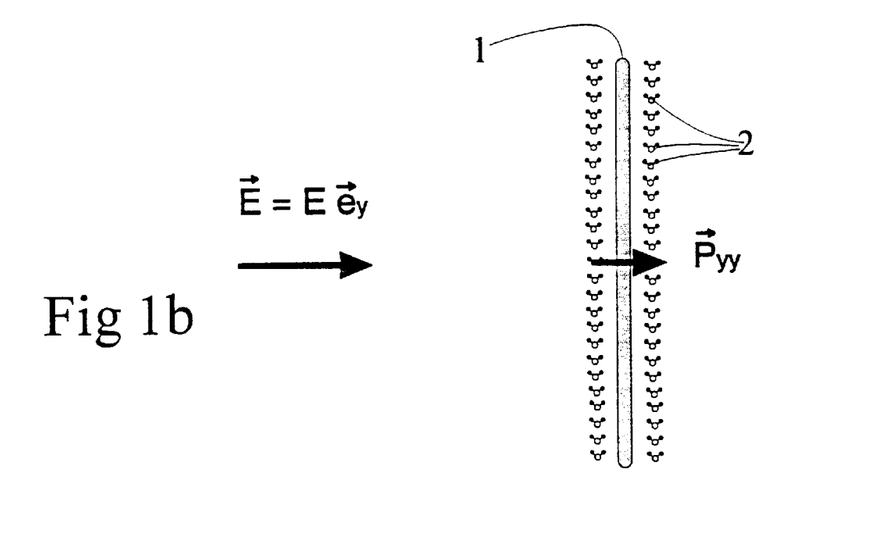
Figure 1C:
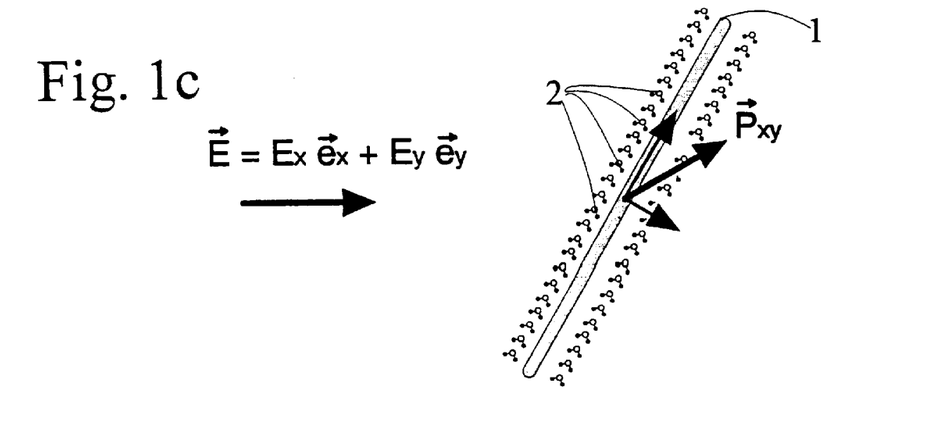

Referring to FIGS. 1a–1c, for reasons of simplicity, the behaviour of a single-cellulosic fiber 1 is examined in an external electric field E. The diameter of the cellulosic fiber 1 is 1–5 μm with a length of 0.5–5 mm. Water molecules 2 are bound on the surface of the fiber 1. Due to its strong dipole character, all the water molecules will align almost invariably in the same manner with respect to the major axis of the fiber 1. When such an aggregate is placed in an external electric field E, its interaction with the external electric field will be strongly dependent on the orientation of the electric field vector E with respect to the fiber 1. The interaction of the water molecules with the electric field reflects the orientation of the fibers 1, because water in the web is chiefly bound on the surface of the fibers 1. When the external electric field vector is oriented parallel to the longitudinal axis of the fiber as shown in FIG. 1a, the water-fiber aggregate induces a much stronger electric polarization vector ($P_{xx}$) than the electric polarization vector ($P_{yy}$) obtained when the external electric field vector is oriented orthogonally to longitudinal axis of the fiber as shown in FIG. 1b. In the intermediate case when the longitudinal axis of the fiber is oriented obliquely to the external electric field vector as shown in FIG. 1c, an electric polarization vector ($P_{xy}$) is obtained with its direction deviated from the direction of the external electric field vector.

In the method according to the present invention, the orientation of the fibers relative to the sensor head of the measurement apparatus need not be changed. An essential characteristic of the method according to the present invention is that fiber orientation is measured by virtue of altering the direction of an external electric field vector E, which is generated by means of a sensor head, relative to the fibers. Simple analysis shows that rotation of the external field vector through a full 360° circle in the plane of the web causes the electric polarization vector of the fibers to induce an electric field vector, which in plane of the web traces an ellipse. The major axis of the ellipse is aligned with the direction of the average orientation of the fibers. The ratio of the axes of the ellipse gives the fiber orientation ratio. The orientation ellipse can be unambiguously determined by three independent measurements.

In a general case, the polarization vector P in a nonisotropic material can be expressed by the formula $$\bar{P} = \epsilon_0 \bar{\bar{\chi}} \bar{E}$$

where $$\bar{\bar{\chi}}$$

is the susceptibility tensor of a nonisotropic material. The components of the susceptibility tensor are complex numbers whose imaginary parts are proportional to the magnitude of the dielectric losses caused by the material in a microwave electromagnetic field. In the two-dimensional case, the formula can be rewritten $$\begin{bmatrix} P_x \\ P_y \end{bmatrix} = \begin{bmatrix} \chi'_{xx} + j\chi''_{xx} & \chi'_{xy} + j\chi''_{xy} \\ \chi'_{yx} + j\chi''_{yx} & \chi'_{yy} + j\chi''_{yy} \end{bmatrix} \begin{bmatrix} E_x \\ E_y \end{bmatrix}$$

By measuring the electric field vector induced by the polarization vector, it is possible to determine a susceptibility tensor in which the real and imaginary parts of its components are proportional to the orientation distribution of the fibers in the paper web. The magnitudes of imaginary parts of the susceptibility tensor components are dependent on both the fibers and the water bound with the fibers. If the measurement frequency is less than 3 GHz, sizing and filler agents contained in a paper or paperboard have a greater effect on the real parts of the tensor than on its imaginary parts. Therefore, determination of the fiber orientation ratio is a more difficult task if the real parts of the susceptibility tensor would be used alone.

According to the present invention, fiber orientation is primarily determined from the imaginary parts of the susceptibility tensor, that is, from the dielectric losses of the material to be measured. As the dielectric losses in paper and paperboard webs are strongly dependent on the amount of bound water, the losses will be nonisotropic according to the orientation distribution of the fibers. This in turn results from the fact that water always is bound on the fiber surface by a single mechanism. As the method is based on the measurement of dielectric losses caused by water bound in the fiber aggregate, it is insensitive to, e.g., internal stresses occurring in the fiber aggregate.

Figure 2A:
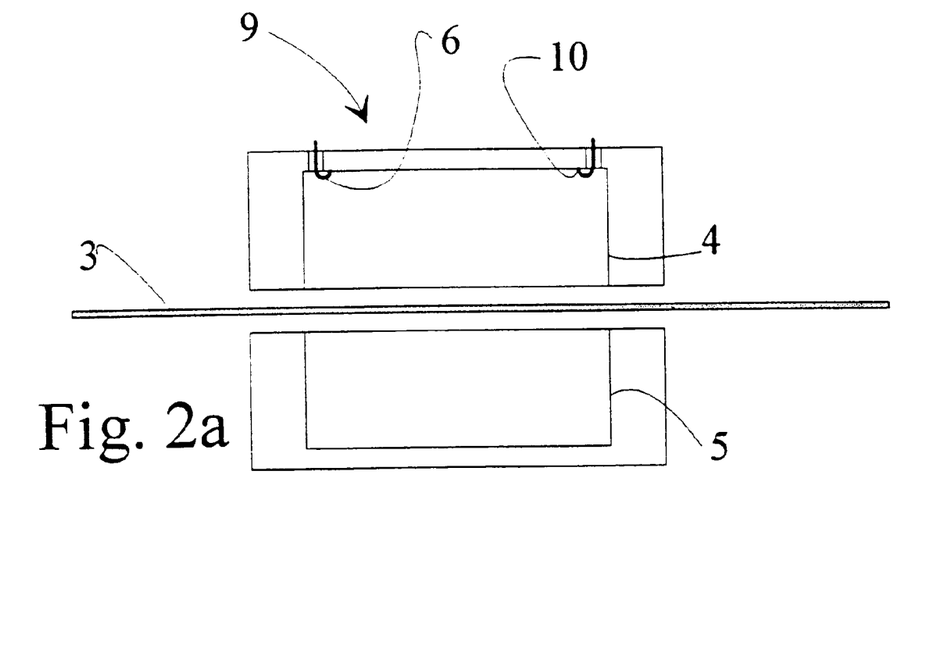
FIG. 2a shows a longitudinally sectional side view of a cavity resonator according to the present invention.
Figure 2B:
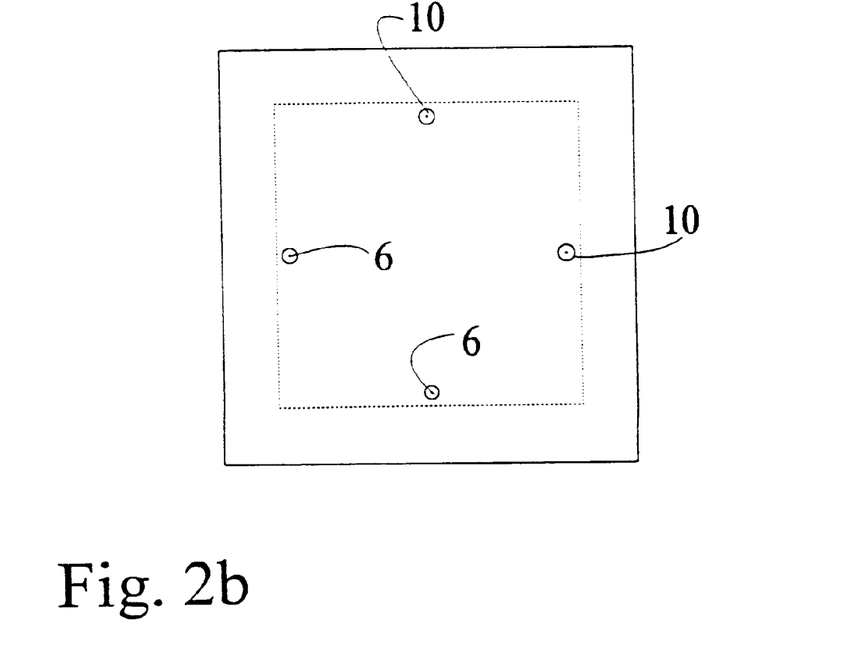

Now referring to FIGS. 2a and 2b, an embodiment according to the present invention is shown therein. A paper web 3 is passed through a split cavity resonator 9. The upper part 4 of the cavity resonator 9 remaining above the web 3 and the lower part 5, remaining below the web, respectively, have a square cross section. Thus, the cavity can support two orthogonal resonant modes with identical resonant frequencies. The electric fields of both modes lie in the plane of the paper web to be measured so that the electric field vector of one mode is oriented in the x-direction while the other is in the y-direction. The upper part of the cavity resonator 9 is provided with four probes 6 and 10 so located that either resonant mode can be excited and measured by means of the probes. As the paper web 3 is passed through the resonator 9, using techniques known in microwave engineering, three parameters are measured: 1) $D_{xx}$ representing the dielectric loss term of the x-direction resonant mode of the electric field, 2) $D_{yy}$ representing the dielectric loss term of the y-direction resonant mode of the electric field and 3) $D_{xy}$ representing the dielectric loss term of the mutual coupling of the x- and y-direction resonant modes. Using conventional mathematical techniques, the main orientation direction and orientation ratio of fibers in the web can be computed from these three parameters. In the present method, $D_{yy}$ and $D_{xx}$ can be obtained by measuring the Q-factors of their respective modes. $D_{xy}$ in turn can be obtained by measuring the imaginary part of the y-direction electric field vector in relation to the x-direction electric field vector using a phase-sensitive detector. Also $D_{yx}$ can be measured using the same method. This arrangement is particularly suitable for use in a situation where the fiber orientation is in either the x- or y-direction. Here, $D_{xy}$ and $D_{yx}$ are small with respect to the main terms $D_{xx}$ and $D_{yy}$. In practice, the method is most applicable to the determination of a small orientation angle. Alternatively, the dielectric losses can be determined by measuring the Q-factors of the resonator in both major directions using conventional microwave measurement techniques. The dielectric loss term $D_{yx}$ of mode cross-coupling can be obtained by measuring the respective Q-factor indirectly from the frequency dependence of the x-direction electric field corrected by the frequency dependence of the exciting electric field in the y-direction. The fiber orientation ratio is also dependent on the web moisture content. Hence, an additional measurement of the z-direction dielectric loss term can be arranged to compensate for the temperature dependence of the method.

Figure 3A:
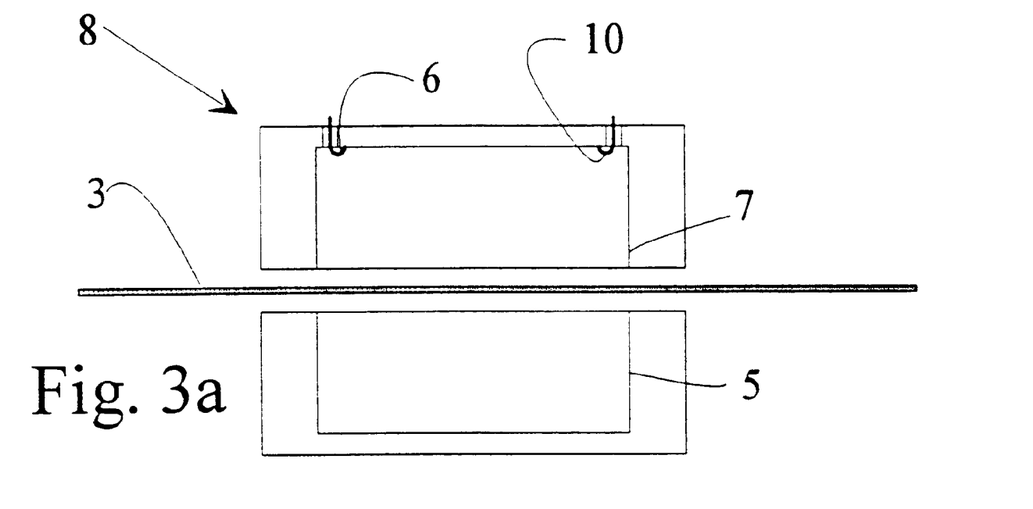
FIG. 3a shows a longitudinally sectional side view of another embodiment of a cavity resonator according to the present invention.
Figure 3B:
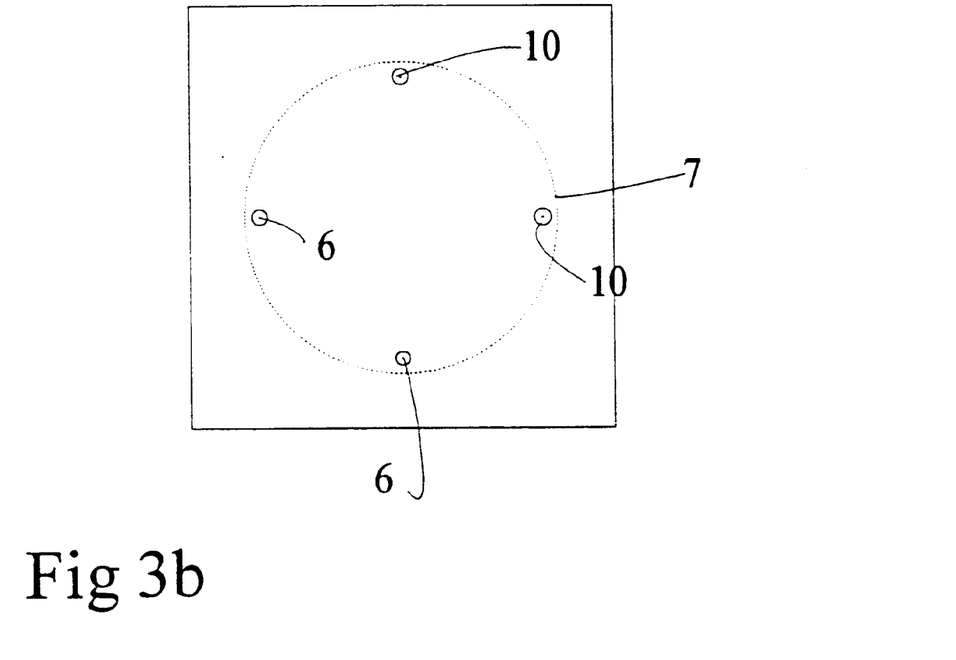

Referring to FIGS. 3a and 3b, an alternative embodiment of the method is shown. Herein, the paper web 3 is arranged to pass through a split cavity resonator 8 having a circular cross section. The cavity resonator is positioned along both sides of the web 3 and is comprised of an upper part 7, which is adapted to both sides and has probes 6, 10 attached thereto, and a lower part 5. This kind of cavity resonator can support an infinite number of resonant modes at the same frequency and having their electric field vectors in a vacant resonator lying in the plane of a fictional paper web 3 (not inserted in the cavity). The resonator is provided with two probes 6 serving to excite the cavity so as to obtain two resonant modes having their electric field vectors oriented orthogonally. Respectively, two measuring probes 10 are provided in the cavity to measure the electric fields of both resonant modes. The exciting probes 6 are fed with a microwave signal in equal phase from a source capable of deviating the signal frequency about the resonant frequency of the cavity. By adjusting the microwave power ratio of the signals feeding the probes, a situation can be created in which the superimposed total electric field of the two modes in the resonator is oriented in a desired direction. In this method, both the resonant frequency and the combined dielectric loss of the two modes excited in the resonator are measured as a function of the angular direction of the total electric field. The angular direction of maximum loss or smallest resonant frequency is pointed in the main orientation direction of the fibers in the web. Respectively, the angular direction of minimum loss or highest resonant frequency occurs in a direction orthogonal to the direction of main orientation. The ratio of the losses in these two orthogonal directions is proportional to the orientation ratio of the paper web, and the fiber orientation angle is thus directly obtained from the angular direction of the total electric field vector at maximum loss or smallest resonant frequency.

In a paper machine equipped for on-line measurement, the resonator halves are typically placed in a traversing measurement carriage which moves the sensor head reciprocatingly across the web in the cross-machine direction. Here, the mutual alignment of the resonator halves may change during the traversing motion, whereby the xy-symmetry of the resonator is violated. In a resonator with a square cross section, this error is evidenced so that the resonant frequencies of the two orthogonal modes initially oscillating at the same frequency assume different resonant frequencies. Similarly, the resonant modes of a resonator with a circular cross section are shifted to separate resonant frequencies even when the resonator does not contain such a paper web that inherently causes asymmetry of the resonant modes due to fiber orientation in the web. If the xy-asymmetry related to the mechanical errors of the traversing motion will not be compensated for, an error of the fiber orientation measurement occurs. Two alternative arrangements can be used to minimize the error:

1) The mutual position of the resonator halves is measured in the xy-plane and alignment of their mutual position is implemented by means of a mechanical or electromagnetic actuator.
2) The mutual position of the resonator halves is measured in the xy-plane and the error caused in the result of the fiber orientation measurement by resonator misalignment is compensated for by computational means. The mutual alignment of the resonator halves in the xy-plane can be measured by inductive, capacitive or optical techniques. Inductive position measurement based on magnetic field is insensitive to soiling (by paper lint, moisture, etc.)

Figure 4:
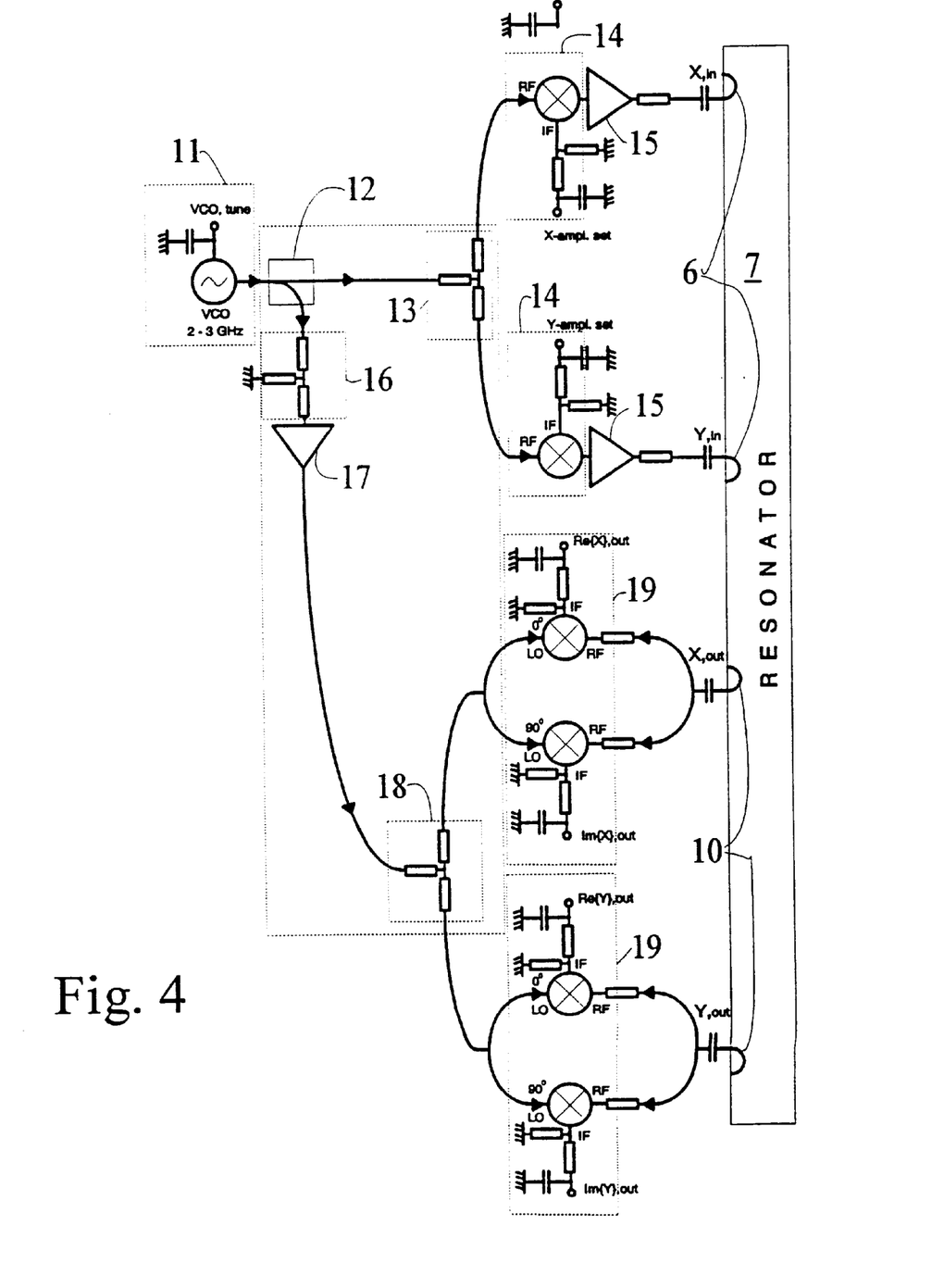
FIG. 4 shows a circuit diagram of a measurement apparatus according to the present invention.

Now referring to FIG. 4, an embodiment of a microwave electronics circuitry for a cavity resonator with circular cross section is shown. In detail, therein a voltage-controlled oscillator (VCO) 11 generates the required microwave power, which is divided into two branches by means of a power splitter 12. A portion of the power is taken via a resistive power divider 13 to two voltage-controlled attenuators (mixers) 14, from which the signals are taken via amplifiers 15 in equal phase to probes 6 exciting the orthogonal modes (x- and y-modes) of the resonator 7. Another portion of the power is taken via an attenuator 16 and an amplifier 17 via a resistive power divider 18 to two quadrature-phase detectors 19, which measure by a phase-lock detection technique both the in-phase (Re) and out-of-phase (Im) electric field vector amplitudes of the two orthogonal electric field modes of the resonator. The microwave electronics circuitry is controlled either using low-frequency control signals generated by analog electronics or digitally by means of a microprocessor. The control electronics section identifies the resonant frequency of the resonator by varying the control input voltage of the VCO 11 and computes the resonator loss from the measured voltages (Re{X}, Im{X}, Re{Y} and Im{Y}) and from the broadening of the resonator frequency response curve. By altering the control voltages at inputs X-ampl.set and Y-ampl.set, the electric field of the resonant mode excited in the cavity can be rotated in any desired direction in the plane of the paper web. Thus, the resonator loss and/or resonant frequency can be measured as a function of the angular direction of the electric field vector.

Figure 5:
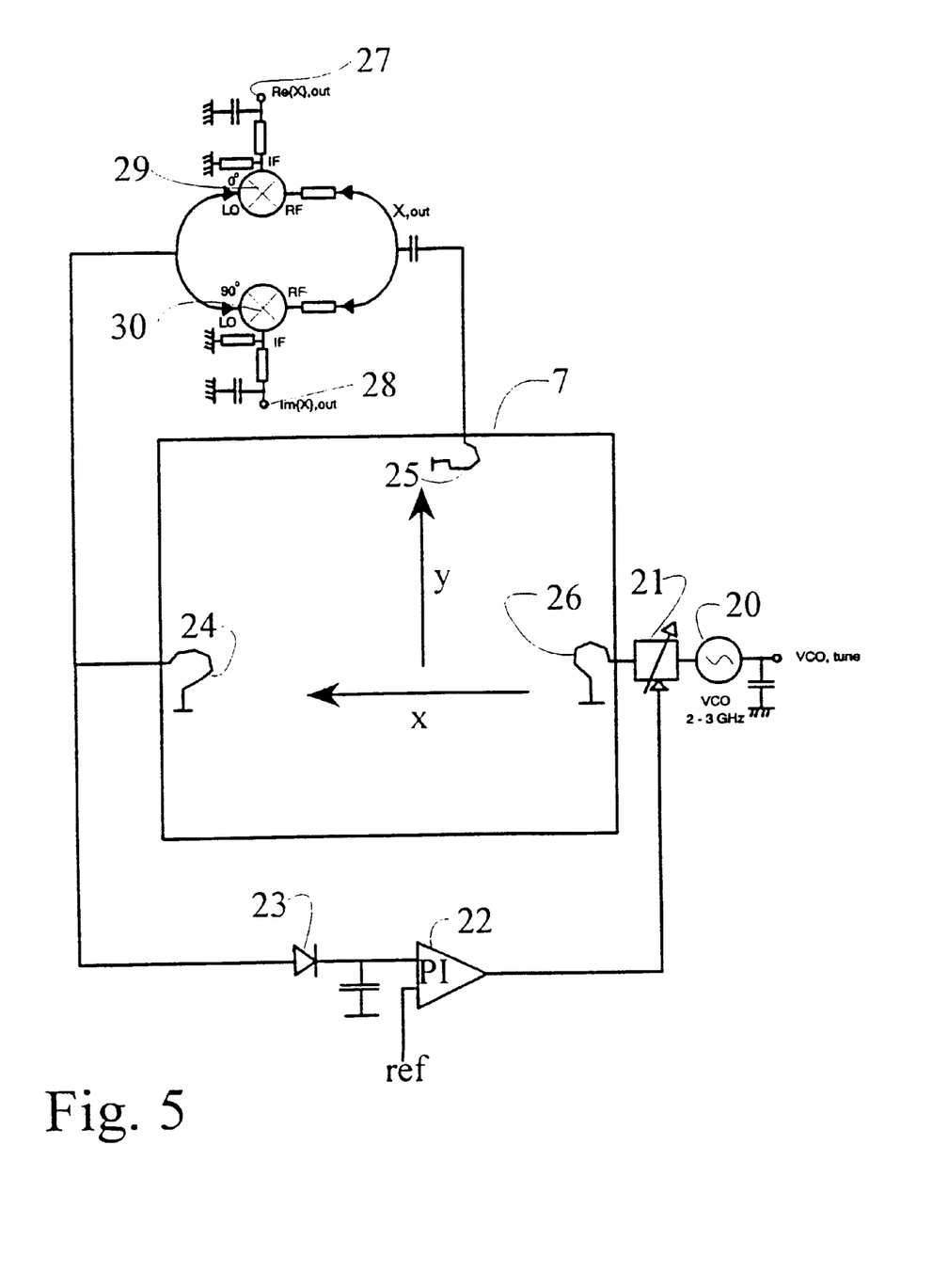
FIG. 5 shows a circuit diagram of another embodiment of a measurement apparatus according to the present invention having the measurement based on the angular direction change of the polarization vector caused in the material under measurement by an external electric field of constant field strength.

Referring to FIG. 5, an alternating electric field of constant field strength can be established by the arrangement shown in the diagram into a cavity resonator 7 by means of a probe 26 fed by an oscillator 20. The field strength is stabilized by a feedback loop comprising a coupling loop 24 grounded at its one end, a diode detector 23 and a PI controller 22 having a set value voltage denoted as ref applied to its other input, whereby the controller output is taken to a voltage-controlled attenuator 21. The angular direction change of the polarization vector caused by the constant-strength electric field in the material under measurement is detected by means of coupling loops 24 and 25. Signals from the coupling loops 24 and 25 are taken to voltage-controlled attenuators 29 and 30, whose outputs 28 and 27 provide information on the angular direction change of the polarization vector, and thus, of the fiber orientation of the material under measurement.

The cavity resonator of square cross section shown in FIGS. 2a and 2b may be replaced by a resonator of rectangular cross section, whereby the measurement arrangement may be modified in the following way. The electric fields of the three lowest-order modes of the resonator 9 lie in the plane of the paper web 3 under measurement oriented as follows: the first mode in the x-direction, the second mode in the y-direction and the third mode radially in the plane of paper web 3 under measurement. Using the above-described techniques, the resonator 9 is used for measuring the losses of the resonant modes, or alternatively, the resonant frequencies of the modes. With the help of three independent measurements, it is again possible to compute the fiber orientation ellipse, wherefrom the fiber orientation angle and orientation ratio can be resolved.

In an embodiment of the method, a split cavity resonator with a circular cross section (see FIGS. 3a and 3b, for instance) is provided with at least three probes for exciting the cavity with microwave power. While the electric fields of the modes excited by each probe lie in the plane of the paper web under measurement, their electric field vectors are in different directions. Using at least three independent measurements (i.e., of loss or resonant frequency), the orientation ellipse may again be determined.

Thus, while there have been shown and described and pointed out fundamental novel features of the present invention as applied to a preferred embodiment thereof, it will be understood that various omissions and substitutions and changes in the form and detailed of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

We claim:

1. An apparatus for determining orientation angle and orientation ratio of fibers in a planar material containing water and comprised of elongated fibers, comprising:

a cavity resonator, the resonator having at least two orthogonal electric field resonant modes, an electric field of a first and a second of the resonant modes lying in a plane of a planar material to be analyzed;

first and second transmitters for generating a modulated electric field in the resonator directed toward a planar material present in the resonator, the electric field being modulated at one of an RF frequency and a microwave frequency, said first and second transmitters being spaced apart from one another within the resonator, said first transmitter transmitting an electric field in the first resonant mode, said second transmitter transmitting an electric field in the second resonant mode the first and second transmitters being positioned to that upon varying power supplied to the transmitters relative to one another an orientation of a total electric field transmitted by the two transmitters is varied;

a means for supplying power to the first and second transmitters to cause each of the transmitters to emit an electric field;

a means for controlling the power supplied by the power supplying means to the first and second transmitters by dividing the power between the first and second transmitters;

first and second receivers for receiving an electric field in said resonator, said first and second receivers being spaced apart from one another within the resonator, said first receiver being positioned to receive a first of the resonant electric field modes said second receiver being positioned to receive a second of the resonant electric field modes; and a means for analyzing signals from said first and second receivers to determine orientation angle and orientation ratio of the fibers in the planar material from the signals from said receivers.

2. The apparatus of claim 1, wherein the source of power is a voltage controlled oscillator.

3. The apparatus of claim 1, wherein the resonator is a cavity resonator.

4. The apparatus of claim 3, wherein the cavity resonator has a square cross section.

5. The apparatus of claim 3, wherein the cavity resonator has a circular cross section.

6. The apparatus of claim 1, wherein said means for controlling the power supplied to the transmitters causes the direction of the electric field to be rotated within the resonator.

7. A method for determining orientation angle and orientation ratio of fibers in a planar material containing water and comprised of elongated fibers, comprising:

(a) introducing a planar material containing water and comprised of elongated fibers into a resonator, the resonator having at least two orthogonal electric field resonant modes, the electric field of a first and a second of the resonant modes lying in a plane of the planar material;

(b) altering the direction of the electric field within the resonator during measurement without altering an orientation of the planar material with respect to the resonator;

(c) measuring the electric field of the two orthogonal resonant modes in the resonator as the electric field is directed toward the planar material;

(d) determining the differences in the electric field caused in step (b); and (e) determining from the difference determined in step (d) an orientation angle and orientation ratio of the fibers in the planar material.

8. The method of claim 7, wherein in said altering step (b) the direction of the electric field is rotated within the resonator.

9. The method of claim 7, wherein the electric field in the resonator is generated by two exciting probes, and wherein in step (b) a power of the electric field directed from one of the two exciting probes is continuously altered relative to a power of the electric field directed from the other of the two exciting probes.

10. The method of claim 9, wherein the power of the electric field directed from the two exciting probes is altered at discrete time intervals.

11. The method of claim 9, wherein said determining step (e) comprises determining losses caused by electric polarization from the planar material.

12. The method of claim 7, wherein the resonator is a cavity resonator.

13. The method of claim 12, further comprising measuring a resonant frequency of the cavity resonator corresponding to the direction of the electric field.

14. The method of claim 12, wherein the cavity resonator has a square cross section.

15. The method of claim 14, wherein the electric field is modulated at an RF frequency.

16. The method of claim 15, wherein the cavity resonator has a square cross section.

17. The method of claim 16, wherein three lowest-order modes of the resonator lie in a plane substantially parallel to the plane of the planar material, a first of the three lowest-order modes being aligned in an x-direction, a second of the three lowest-order modes being aligned in a y-direction, and a third of the lowest-order modes being radially aligned, and wherein in said step (d) a difference of the three lowest-order modes is determined.

18. The method of claim 12, wherein the cavity resonator has a circular cross section.

19. The method of claim 18, wherein the electric field in the resonator is generated by two exciting probes, and wherein in step (b) a power of the electric field directed from one of the two exciting probes is continuously altered relative to a power of the electric field directed from the other of the two exciting probes.

20. The method of claim 19, wherein said step (b) further comprises directing a modulated electric field from a third exciting probe toward the planar material in the resonator, the electric field directed from the third exciting probe being modulated at one of an RF frequency and a microwave frequency and being directed toward the planar material, wherein each of the three exciting probes is excited sequentially.

21. The method of claim 7, wherein the measuring in step (c) is controlled using one of low-frequency analog control signals generated by analog electronics and digital control signals generated by a digital microprocessor.

22. The method of claim 21, wherein said controlling further comprises measuring the resonant frequency of the resonator.

23. The method of claim 22, wherein said controlling comprises computing resonator loss and, in response to such resonator loss measurement, varying the modulated electric field in an angular direction in a plane of the planar material, and wherein said determining step (d) determines orientation angle and orientation ratio of the fibers in the planar material as a function of the angular direction of the electric field.

24. The method of claim 12, further comprising measuring the relative positions of halves of the cavity resonator to determine alignment of the cavity resonator halves, and wherein said determining step (d) further comprises compensating for any misalignment of the halves of the cavity resonator.

* * * * *